(12) United States Patent
Sakuma et al.

(10) Patent No.: US 8,778,933 B2
(45) Date of Patent: *Jul. 15, 2014

(54) DIAZEPINEDIONE DERIVATIVE

(71) Applicant: Nippon Chemiphar Co., Ltd., Tokyo (JP)

(72) Inventors: Shogo Sakuma, Misato (JP); Toshihiro Takahashi, Misato (JP); Masatoshi Ushioda, Misato (JP); Toshiyasu Imai, Misato (JP); Kazuhike Inoue, Fukuoka (JP)

(73) Assignee: Nippon Chemiphar Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/921,382

(22) Filed: Jun. 19, 2013

(65) Prior Publication Data

US 2013/0281441 A1    Oct. 24, 2013

Related U.S. Application Data

(63) Continuation of application No. 13/148,728, filed as application No. PCT/JP2010/052571 on Feb. 15, 2010, now Pat. No. 8,470,814.

(30) Foreign Application Priority Data

Feb. 16, 2009   (JP) ................. 2009-032705

(51) Int. Cl.
*A61K 31/5513* (2006.01)
*A61P 25/04* (2006.01)
*C07D 413/10* (2006.01)
*C07D 403/10* (2006.01)
*C07D 243/10* (2006.01)

(52) U.S. Cl.
CPC ............ *C07D 243/10* (2013.01); *C07D 413/10* (2013.01); *C07D 403/10* (2013.01)
USPC ........................................................ 514/220

(58) Field of Classification Search
USPC ........................................................ 514/220
See application file for complete search history.

(56) References Cited

U.S. PATENT DOCUMENTS

2005/0074819 A1    4/2005 Inoue et al.

*Primary Examiner* — Bruck Kifle
(74) *Attorney, Agent, or Firm* — Nixon Peabody LLP; Jeffery L. Costellia

(57) ABSTRACT

A diazepinedione derivative represented by the formula (I) or a pharmacologically acceptable salt thereof is used as a $P2X_4$ receptor antagonist:

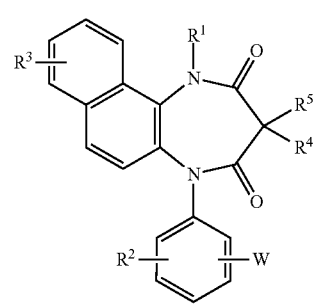

(I)

wherein $R^1$ represents a hydrogen atom, an alkyl group having 1 to 8 carbon atoms, or the like, $R^2$ and $R^3$ represent a hydrogen atom, an alkyl group having 1 to 8 carbon atoms, a halogen atom, or the like, $R^4$ and $R^5$ represent a hydrogen atom, an alkyl group having 1 to 8 carbon atoms, or the like, and W represents tetrazole or the like.

4 Claims, No Drawings

DIAZEPINEDIONE DERIVATIVE

FIELD OF THE INVENTION

The present invention relates to a diazepinedione derivative showing P2X$_4$ receptor antagonism.

BACKGROUND OF THE INVENTION

ATP receptors are basically classified into P2X family of ion-channel type receptors and P2Y family of G protein-coupled receptors. Until now, there are reported, respectively, seven sub-types (P2X$_{1-7}$) and eight sub-types (P2Y$_{1, 2, 4, 6, 11-14}$).

It has been reported that P2X$_4$ receptor (Genebank No. X87763), which is a sub-type of P2X family, is present widely in the central nervous systems. See the following documents:
Non-patent document 1: Buell, et al. (1996) EMBO J. 15: 55-62;
Non-patent document 2: Seguela, et al. (1996) J. Neurosci. 16: 448-455;
Non-patent document 3: Bo, et al. (1995) FEBS Lett. 375: 129-133;
Non-patent document 4: Soto, et al. (1996) Proc. Natl. Acad. Sci. USA 93: 3684-3788; and
Non-patent document 5: Wang, et al. (1996) Biochem. Res. Commun. 220: 196-202.

The mechanism of pathogenesis of intractable pains such as neuropathic pain is unclear. Therefore, if non-steroidal anti-inflammatory drugs (NSAIDs) and morphine are not effective, there is no other pharmacotherapy. In that case, the patient and surrounding people take up a heavy burden in mind and body. The neuropathic pain is caused by injury of peripheral or central nervous systems, for instance, post-surgery pain, cancer, spinal cord injury, herpes zoster, diabetic neuritis, or trigeminal neuralgia.

Recently, Inoue, et al. studied the involvement of P2X receptors in neuropathic pain using dorsal root ganglion neuron-injured animal model which induces allodynia, and indicated that the nerve-injured pain (particularly, allodynia) is caused via P2X$_4$ receptors on spinal microglia. See the following documents:
Non-patent document 6: M. Tsuda, et al. (2003) Nature, 424, 778-783;
Non-patent document 7: Jeffrey A. M. Coull, et al. (2005) Nature, 438, 1017-1021; and
Patent document 1: United States patent publication No. 20050074819.

Accordingly, compounds that inhibit the action of P2X$_4$ receptors are expected to be employed for preventing or treating nociceptive, inflammatory, and neuropathic pains.

WO 2004/085440 (Patent document 2) discloses that benzofuro-1,4-diazepin-2-one derivatives having the below-illustrated formula (A) show P2X$_4$ receptor antagonism:

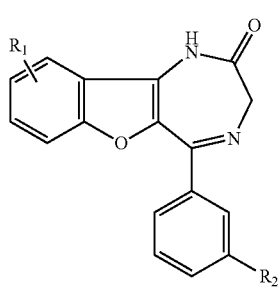

(A)

wherein R$_1$ is halogen, and R$_2$ is hydrogen, halogen, nitro, cyano, C(O)—OR$_3$, C(O)—NR$_4$R$_5$, SO$_2$—OR$_3$, or SO$_2$—NR$_4$R$_5$, or in which R$^1$ is hydrogen, and R$_2$ is halogen, nitro, cyano, C(O)—OR$_3$, C(O)—NR$_4$R$_5$, SO$_2$—OR$_3$, or SO$_2$—NR$_4$R$_5$.

The present inventors have found 1,4-diazepin-2-on derivatives showing P2X$_4$ receptor antagonism, and filed the following patent applications:
Patent document 3: WO 2007/072974
Patent document 4: WO 2007/074940
Patent document 5: WO 2008/023847
Japanese Patent Publication No. 2 (1990)-30443 (Patent document 6) discloses compounds represented by the following formula (C):

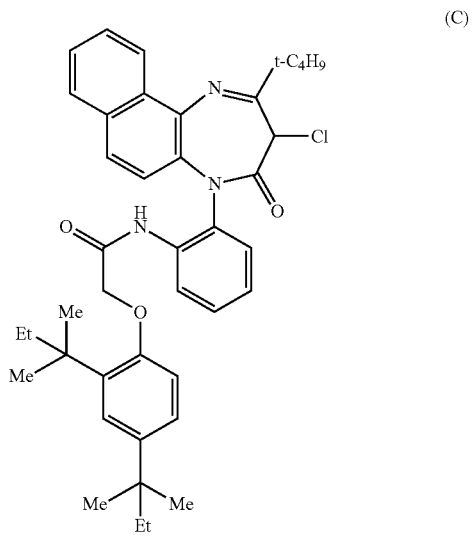

(C)

Patent document 6 describes that the compounds represented by the formula (C) can be used as photographic couplers. Patent document 6, however, is silent with respect to the relation between these compounds and the P2X$_4$ receptor antagonism.

DISCLOSURE OF THE INVENTION

It is the object of the present invention to provide a diazepinedione derivative represented by the formula (I), which shows P2X$_4$ receptor antagonism.

The present invention relates to a diazepinedione derivative having the following formula (I) or a pharmacologically acceptable salt thereof:

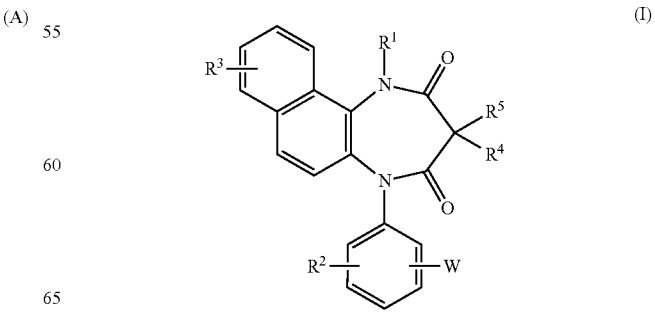

(I)

wherein $R^1$ represents a hydrogen atom, an alkyl group having 1 to 8 carbon atoms, an alkenyl group having 2 to 8 carbon atoms, an alkyl group having 1 to 8 carbon atoms substituted with 1 to 3 halogen atoms, or an alkyl group having 1 to 3 carbon atoms substituted with phenyl;

each of $R^2$ and $R^3$ independently represents a hydrogen atom, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a halogen atom, hydroxyl, nitro, cyano, amino, an alkylamino group having 1 to 8 carbon atoms, a dialkylamino group having 2 to 8 carbon atoms, an acylamino group having 2 to 8 carbon atoms, an acylamino group having 2 to 8 carbon atoms substituted with 1 to 3 halogen atoms, an alkylsulfonylamino group having 1 to 8 carbon atoms, carboxyl, an acyl group having 2 to 8 carbon atoms, an alkoxycarbonyl group containing an alkoxy moiety having 1 to 8 carbon atoms, carbamoyl, an alkylthio group having 1 to 8 carbon atoms, an alkylsulfinyl group having 1 to 8 carbon atoms, an alkylsulfonyl group having 1 to 8 carbon atoms, or sulfamoyl;

each of $R^4$ and $R^5$ independently represents a hydrogen atom, an alkyl group having 1 to 8 carbon atoms, an alkyl group having 1 to 8 carbon atoms substituted with 1 to 3 halogen atoms, or an alkyl group having 1 to 3 carbon atoms substituted with phenyl; and W represents a five or six membered heterocyclic ring containing 1 to 4 nitrogen atoms as the members of the ring, and optionally having a substituent.

The invention also relates to a P2X$_4$ receptor antagonist containing a diazepinedione derivative represented by the formula (I) or its pharmacologically acceptable salt as an active ingredient.

The invention further relates to a preventive or therapeutic agent for neuropathic pains containing a diazepinedione derivative represented by the formula (I) or its pharmacologically acceptable salt as an active ingredient.

THE BEST MODE OF THE INVENTION

The present invention is described below in more detail.

In the compound of the present invention represented by the formula (I), the alkyl group having 1 to 8 carbon atoms for $R^1$, $R^2$, $R^3$, $R^4$, and $R^5$ can be methyl, ethyl, propyl, isopropyl, butyl, isobutyl, t-butyl, pentyl, or hexyl.

The alkenyl group having 2 to 8 carbon atoms for $R^1$ can be allyl.

The alkyl group having 1 to 8 carbon atoms substituted with 1 to 3 halogen atoms for $R^1$, $R^2$, $R^3$, $R^4$, and $R^5$ can be methyl, ethyl, propyl, isopropyl, butyl, or t-butyl substituted with 1 to 3 halogen atoms such as 1 to 3 fluoro, chloro, or bromo atoms, and preferably is trifluoromethyl, chloromethyl, 2-chloroethyl, 2-bromoethyl, or 2-fluoroethyl.

The alkyl group having 1 to 3 carbon atoms substituted with phenyl for $R^1$, $R^4$, and $R^5$ can be benzyl.

The alkoxy group having 1 to 8 carbon atoms for $R^2$ and $R^3$ can be methoxy, ethoxy, propoxy, isopropoxy, butoxy, isobutoxy, t-butoxy, pentyloxy, or hexyloxy.

The alkoxy group having 1 to 8 carbon atoms substituted with 1 to 3 halogen atoms for $R^2$ and $R^3$ can be methyl, ethyl, propyl, isopropyl, butyl, or t-butyl substituted with 1 to 3 halogen atoms such as 1 to 3 fluoro, chloro, or bromo atoms, and preferably include trifluoromethoxy, 2-chloroethoxy, 2-bromoethoxy, or 2-fluoroethoxy.

The halogen atom for $R^2$ and $R^3$ can be fluoro, chloro, and bromo atoms.

The alkylamino group having 1 to 8 carbon atoms for $R^2$ and $R^3$ can be methylamino or ethylamino.

The dialkylamino group having 1 to 8 carbon atoms for $R^2$ and $R^3$ can be dimethylamino or diethylamino.

The acylamino group having 2 to 8 carbon atoms for $R^2$ and $R^3$ can be acetylamino.

The acylamino group having 2 to 8 carbon atoms substituted with 1 to 3 halogen atoms for $R^2$ and $R^3$ can be trifluoromethylcarbonylamino.

The alkylsulfonylamino group having 1 to 8 carbon atoms for $R^2$ and $R^3$ can be methylsulfonylamino.

The acyl group having 2 to 8 carbon atoms for $R^2$ and $R^3$ can be acetyl.

The alkoxycarbonyl group containing an alkoxy moiety having 1 to 8 carbon atoms for $R^2$ and $R^3$ can be methoxycarbonyl, or ethoxycarbonyl.

The alkylthio group having 1 to 8 carbon atoms for $R^2$ and $R^3$ can be methylthio.

The alkylsulfinyl group having 1 to 8 carbon atoms for $R^2$ and $R^3$ can be methylsulfinyl.

The alkylsulfonyl group having 1 to 8 carbon atoms for $R^2$ and $R^3$ can be methylsulfonyl.

The five or six membered heterocyclic ring containing 1 to 4 nitrogen atoms as the members of the ring, and optionally having a substituent for W can be tetrazole, 1,2,4-triazole, 1,2,3-triazole, 1,2,4-oxadiazole, pyrazole, imidazole, oxazole, isoxiazole, pyrrole, thiazole, pyridine, and pyrrolidine.

The substituent of the five or six membered heterocyclic ring containing 1 to 4 nitrogen atoms as the members of the ring, and optionally having a substituent for W can be an alkyl group having 1 to 8 carbon atoms (such as methyl, ethyl), an alkyl group having 1 to 8 carbon atoms substituted with 1 to 3 halogen atoms (such as trifluoromethyl), a halogen atom (such as fluoro atom), cyano, oxo, or thioxo.

$R^2$ or $R^3$ in the formula (I) can be same or different 1 to 3 substituents attached to the benzene rings.

The compound of the present invention of the formula (I) preferably is the following compound.

(1) A diazepinedione derivative having the formula (I) or a pharmacologically acceptable salt thereof, wherein W is tetrazole, 1,2,4-triazole, 1,2,3-triazole, 1,2,4-oxadiazole, pyrazole, or imidazole optionally having a substituent selected from a group consisting of an alkyl group having 1 to 8 carbon atoms, an alkyl group having 1 to 8 carbon atoms substituted with 1 to 3 halogen atoms, a halogen atom, cyano, oxo, and thioxo.

(2) A diazepinedione derivative having the formula (I) or a pharmacologically acceptable salt thereof, wherein W is tetrazole, 1,2,4-triazole, or 1,2,3-triazole optionally having a substituent selected from a group consisting of an alkyl group having 1 to 8 carbon atoms, an alkyl group having 1 to 8 carbon atoms substituted with 1 to 3 halogen atoms, a halogen atom, and cyano.

(3) A diazepinedione derivative having the formula (I) or a pharmacologically acceptable salt thereof, wherein W is 5-oxo-1,2,4-oxadiazole or 5-thioxo-1,2,4-oxadiazole.

(4) A diazepinedione derivative having the formula (I) or a pharmacologically acceptable salt thereof, wherein W is tetrazole.

(5) A diazepinedione derivative defined in any one of the formula (I) and (1) to (4) or a pharmacologically acceptable salt thereof, wherein $R^1$ is a hydrogen atom or an alkyl group having 1 to 8 carbon atoms.

(6) A diazepinedione derivative defined in any one of the formula (I) and (1) to (3) or a pharmacologically acceptable salt thereof, wherein $R^1$ is a hydrogen atom.

(7) A diazepinedione derivative defined in any one of the formula (I) and (1) to (6) or a pharmacologically acceptable salt thereof, wherein $R^4$ is a hydrogen atom, and $R^5$ is a hydrogen atom or an alkyl group having 1 to 8 carbon atoms.

(8) A diazepinedione derivative defined in any one of the formula (I) and (1) to (6) or a pharmacologically acceptable salt thereof, wherein each of $R^4$ and $R^5$ is a hydrogen atom.

(9) A diazepinedione derivative defined in any one of the formula (I) and (1) to (8) or a pharmacologically acceptable salt thereof, wherein $R^2$ is a hydrogen atom, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a halogen atom, hydroxyl, nitro, cyano, amino, carboxyl, an acyl group having 2 to 8 carbon atoms, or an alkoxycarbonyl group containing an alkoxy moiety having 1 to 8 carbon atoms.

(10) A diazepinedione derivative defined in any one of the formula (I) and (1) to (8) or a pharmacologically acceptable salt thereof, wherein $R^2$ is a hydrogen atom.

(11) A diazepinedione derivative defined in any one of the formula (I) and (1) to (10) or a pharmacologically acceptable salt thereof, wherein $R^3$ is a hydrogen atom, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, a halogen atom, hydroxyl, nitro, cyano, amino, carboxyl, an acyl group having 2 to 8 carbon atoms, or an alkoxycarbonyl group containing an alkoxy moiety having 1 to 8 carbon atoms.

(12) A diazepinedione derivative defined in any one of the formula (I) and (1) to (10) or a pharmacologically acceptable salt thereof, wherein $R^3$ is a hydrogen atom.

The pharmacologically acceptable salts of the compound represented by the formula (I) include a hydrochloride salt when $R^2$, $R^3$ in the formula (I) is amino or the like. The salts also include an alkali metal (e.g., sodium, potassium, lithium) salt when $R^2$, $R^3$ in the formula (I) is carboxyl.

The compound of the present invention can be a geometrical isomer or an optical isomer such as an optically active substance and racemic modification, each of which is included within the scope of the invention.

The schemes for synthesis of the compound represented by the formula (I) are shown below.

[Method 1]

(First step)

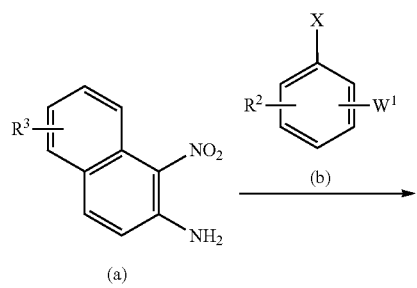

(Second step)

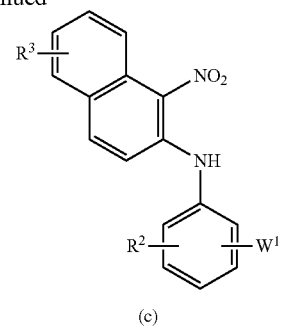

(c) →

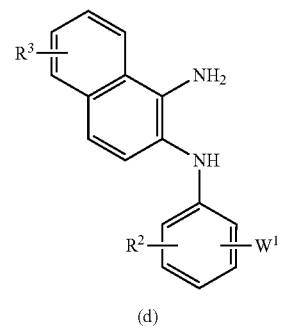

(Third step)

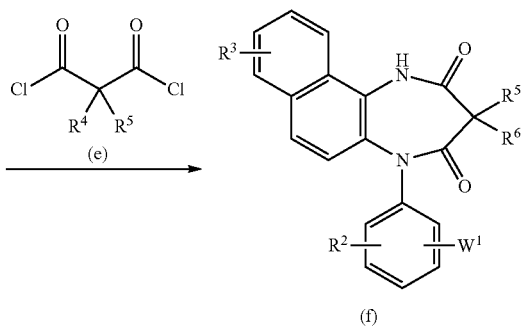

$R^1 = H$

In the above-illustrated formulas, X represents a halogen atom such as a bromo atom, $W^1$ is the same as W, and $R^2$, $R^3$, $R^4$, and $R^5$ are defined above.

In the first step, the compound of the formula (c) can be obtained by a way of a coupling reaction of a compound of the formula (a) with a compound of the formula (b) using a palladium catalyst or the like in the presence of a base such as cesium carbonate, potassium carbonate in an inert solvent such as toluene, tert-butanol.

In the second step, the compound of the formula (d) can be obtained by reduction of a compound of the formula (c) in an inert solvent such as THF, methanol, chloroform, or acetic acid. The reduction can be conducted with iron, tin(II) chloride, zinc, or in the presence of a catalyst such as palladium-carbon.

In the third step, the compound of the present invention represented by the formula (f) can be obtained by a reaction of the compound of the formula (d) with the compound of the formula (e) optionally in the presence of a base in an inert solvent such as toluene or THF. In the case that W is tetrazole having a protective group, the compound of the present invention (wherein $R^1$=H) represented by the formula (I) can be obtained by deblocking the compound of the formula (f).

[Method 2]

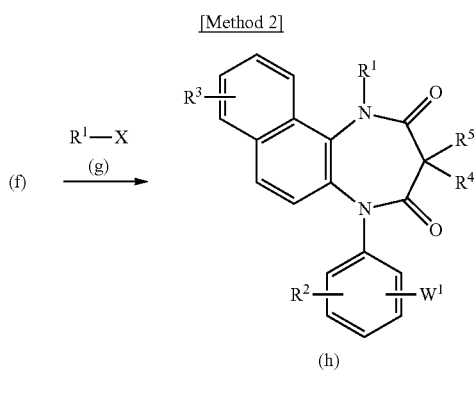

$R^1 \neq H$

In the above-illustrated formulas, X represents a halogen atom such as a bromo, chloro, or iodo atom, $W^1$ is the same as W, and $R^1$, $R^2$, $R^3$, $R^4$, and $R^5$ are defined above.

The compound of the present invention represented by the formula (h) can be obtained by a reaction of the compound of the formula (f) with the compound of the formula (g) in the presence of a base such as sodium hydride in an inert solvent such as dimethyl sulfoxide.

[Method 3]

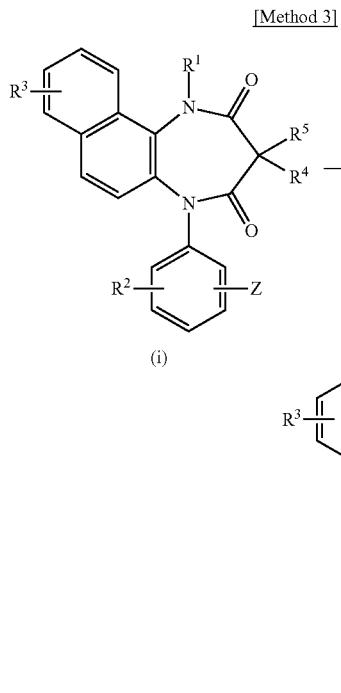

In the above-illustrated formulas, Z represents formyl, cyano, carboxyl, an alkoxycarbonyl group, a halogen atom, or amino, and $R^1$, $R^2$, $R^3$, $R^4$, $R^5$, and W are defined above.

The compound of (j) can be obtained by reacting the compound of (i) with a reagent capable of converting the moiety of Z into W, as is described below.

(1) W: tetrazol-5-yl

The compound of (j) can be obtained by reacting the compound of (i) in which Z is cyano with tri-n-butyltin azide followed by treatment with an acid.

(2) W: tetrazol-1-yl

The compound of (j) can be obtained by reacting the compound of (i) in which Z is amino with ethyl orthoformate and sodium azide.

(3) W: (1,2,4-triazol)-1-yl

The compound of (j) can be obtained by reacting the compound of (i) in which Z is bromo atom with 1,2,4-triazole.

(4) W: (1,2,3-triazol)-4-yl

The compound of (j) can be prepared by condensing the compound of (i) in which Z is formyl with methylphenyl sulfone under a basic condition, and then reacting the obtained product (a vinyl sulfone derivative) with sodium azide.

The compound of the present invention represented by formula (I) can also be prepared by referring to the below described Examples and the patent documents described above and the other known documents.

Examples of the obtained compounds of the present invention are shown in the following Tables 1 to 8.

(Representative compound I)

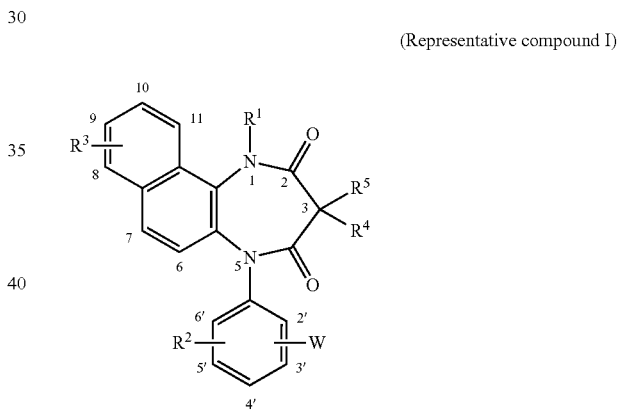

In the above-illustrated formula, each of $R^2$ and $R^3$ is a hydrogen atom, $R^1$, $R^4$, $R^5$, W, and the substitution position of W are shown in Tables 1 to 3.

TABLE 1

| $R^1$ | Position of W | W | $R^4/R^5$ |
| --- | --- | --- | --- |
| H | 2- | 1H-tetrazol-5-yl | H/H |
| H | 3- | 1H-tetrazol-5-yl | H/H |
| H | 3- | (1-methyl-1H-tetrazol)-5-yl | H/H |
| H | 4- | 1H-tetrazol-5-yl | H/H |
| $CH_3$ | 3- | 1H-tetrazol-5-yl | H/H |
| $CH_3$ | 3- | 1H-tetrazol-5-yl | $CH_3$/H |
| benzyl | 3- | 1H-tetrazol-5-yl | H/H |
| H | 3- | 1H-tetrazol-1-yl | H/H |
| H | 3- | 1H-tetrazol-1-yl | $CH_3$/$CH_3$ |
| H | 3- | (1,2,3-triazol)-5-yl | H/H |
| H | 3- | (1,2,4-triazol)-3-yl | H/H |
| H | 4- | (1,2,4-triazol)-3-yl | H/H |

TABLE 2

| R¹ | Position of W | W | R⁴/R⁵ |
|---|---|---|---|
| H | 2- | (1,2,4-triazol)-1-yl | H/H |
| H | 3- | (1,2,4-triazol)-1-yl | H/H |
| H | 3- | [5-(trifluoromethyl)-1,2,4-triazol]-3-yl | H/H |
| H | 3- | [5-(trifluoromethyl)-1,2,4-triazol]-3-yl | ethyl/H |
| H | 3- | [5-fluoro-1,2,3-triazol]-4-yl | H/H |
| H | 3- | [5-fluoro-1,2,3-triazol]-4-yl | $CH_3/CH_3$ |
| H | 3- | [5-cyano-1,2,3-triazol]-4-yl | H/H |
| H | 4- | 1H-imidazol-1-yl | H/H |
| H | 4- | 1H-imidazol-1-yl | Pr/H |
| H | 3- | 1H-imidazol-2-yl | H/H |
| H | 3- | 1H-imidazol-4-yl | H/H |
| H | 3- | imidazolin-2-yl | H/H |

TABLE 3

| R¹ | Position of W | W | R⁴/R⁵ |
|---|---|---|---|
| H | 2- | pyrazol-3-yl | H/H |
| H | 3- | pyrazol-4-yl | H/H |
| H | 3- | pyrazol-5-yl | $CH_3/H$ |
| H | 3- | (1,2,4-oxadiazol)-3-yl | H/H |
| H | 3- | (1,3,4-oxadiazol)-2-yl | H/H |
| H | 3- | (5-oxo-1,2,4-oxadiazol)-3-yl | H/H |
| H | 3- | pyrrol-1-yl | H/H |
| H | 4- | pyrrolidin-2-yl | H/H |
| $CH_3$ | 4- | pyrrolidin-2-yl | $CH_3/H$ |
| H | 4- | (1,3-oxazol)-5-yl | H/H |
| H | 3- | (1,3-oxazol)-5-yl | H/H |
| H | 2- | (1,3-thiazol)-5-yl | H/H |

(Representative compound II)

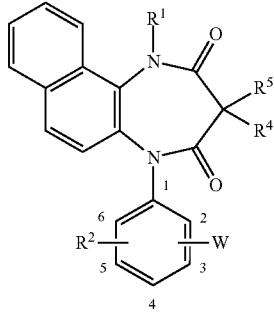

In the above-illustrated formula, R¹, R², R⁴, R⁵, W, and the substitution position of W are shown in Tables 4 and 5.

TABLE 4

| R¹ | R² | Position of W | W | R⁴/R⁵ |
|---|---|---|---|---|
| H | 4-OH | 3- | 1H-tetrazol-5-yl | H/H |
| H | 4-$OCH_3$ | 3- | 1H-tetrazol-5-yl | H/H |
| $CH_3$ | 2-Cl | 3- | 1H-tetrazol-5-yl | H/H |
| H | 2,6-Cl | 3- | 1H-tetrazol-5-yl | H/H |
| H | 4-F | 3- | 1H-tetrazol-5-yl | H/H |
| H | 4-Br | 3- | 1H-tetrazol-5-yl | ethyl/H |
| H | 3-$OCH_3$ | 4- | (1-methyl-1H-tetrazol)-5-yl | H/H |
| H | 4-$CH_3$ | 3- | 1H-tetrazol-5-yl | H/H |

TABLE 5

| R¹ | R² | Position of W | W | R⁴/R⁵ |
|---|---|---|---|---|
| H | 4-Cl | 3- | (1,2,3-triazol)-5-yl | $CH_3/H$ |
| H | 4-$CF_3$ | 3- | (1,2,3-triazol)-5-yl | H/H |
| H | 3-$SCH_3$ | 4- | (1,2,4-triazol)-1-yl | H/H |
| H | 3-$SO_2CH_3$ | 4- | 1H-imidazol-1-yl | H/H |
| H | 3-$NHSO_2CH_3$ | 4- | 1H-imidazol-1-yl | H/H |
| H | 4-$OCH_3$ | 3- | 1H-imidazol-4-yl | H/H |
| H | 4-F | 2- | pyrazol-3-yl | H/H |

(Representative compound III)

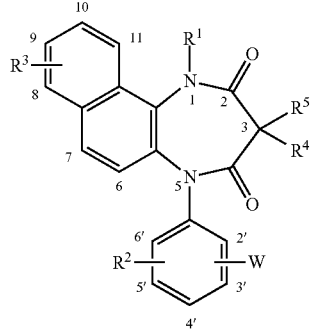

In the above-illustrated formula, R¹, R², R³, R⁴, R⁵, W, and the substitution position of W are shown in Tables 6 and 7.

TABLE 6

| R¹ | R² | Position of W | W | R³ | R⁴/R⁵ |
|---|---|---|---|---|---|
| H | H | 3- | 1H-tetrazol-5-yl | 9-Br | H/H |
| H | 4-$OCH_3$ | 3- | 1H-tetrazol-5-yl | 9-Cl | H/H |
| H | 4-OH | 3- | 1H-tetrazol-5-yl | 10-$OCH_3$ | H/H |
| H | 2-Cl | 3- | 1H-tetrazol-5-yl | 9-Br | H/H |
| H | 2,6-Cl | 3- | 1H-tetrazol-5-yl | 9-$CH_3$ | H/H |
| H | H | 3- | 1H-tetrazol-5-yl | 10-Cl | $CH_3/H$ |
| H | 3-$OCH_3$ | 4- | (1-methyl-1H-tetrazol)-5-yl | 9-$CF_3$ | H/H |

TABLE 7

| R¹ | R² | Position of W | W | R³ | R⁴/R⁵ |
|---|---|---|---|---|---|
| H | 4-$CH_3$ | 3- | 1H-tetrazol-1-yl | 9-CN | Pr/H |
| $CH_3$ | H | 3- | (1,2,3-triazol)-5-yl | 9-OH | H/H |
| ethyl | H | 3- | (1,2,3-triazol)-5-yl | 10-F | H/H |
| H | 3-Br | 4- | (1,2,4-triazol)-1-yl | 9-$SCH_3$ | H/H |
| allyl | H | 4- | 1H-imidazol-1-yl | 8-$OCH_3$ | H/H |
| H | H | 3- | 1H-imidazol-1-yl | 10-$OCH_3$ | $CH_3/CH_3$ |

The pharmacological effects of the present invention are described below.

$P2X_4$ antagonism of the compound of the present invention is measured as described below.

1321N1 cells stably expressing human $P2X_4$ receptors were adopted for calcium influx assay. P2X4/1321N1 cells were plated in 96-well assay plate and cultured 24 hours in an atmosphere of 5% $CO_2$ at 37° C. Fura-2 AM calcium indicator dissolved in an extracellular solution for calcium imaging was loaded onto cells for 45 minutes at room temperature. The fluorescence was detected by FLUOstar Optima micro plate reader (BMG labtech). The cells were alternatively illuminated with two excitations wavelengths (340 nm and 380 nm) via xenon lamp and the emitted fluorescence was measured at 510 nm. The fluorescence changes after the treatment of 1 μM ATP were monitored and determined the fluorescence ratio ($F_{340}/F_{380}$) as the index of intracellular calcium change. Tested compounds were treated to cells 15 min before the addition of ATP and the inhibition activities of compounds were calculated by comparing the $Ca^{2+}$ response with control in the absence of tested compound.

As is evident from the below-described results shown in Example 17, the compound of the present invention shows excellent $P2X_4$ receptor antagonism.

Therefore, it is considered that the diazepinedione derivative represented by the formula (I) or its pharmacologically acceptable salt, which shows $P2X_4$ receptor antagonism, is effective as an agent for prevention or treatment of nociceptive, inflammatory, and neuropathic pains. In more detail, it is effective as a preventive or therapeutic agent for pains caused by various cancers, diabetic neuritis, viral diseases such as herpes, and osteoarthritis. The preventive or therapeutic agent of the present invention can also be used in combination with other agents such as opioid analgesic (e.g., morphine, fentanyl), sodium channel inhibitor (e.g., novocaine, lidocaine), or NSAIDs (e.g., aspirin, ibuprofen). The agent for pains caused by cancers can be used in combination with a carcinostatic such as a chemotherapic.

The compound of the present invention can be administered to human beings by ordinary administration methods such as oral administration or parenteral administration.

The compound can be granulated in ordinary manners for the preparation of pharmaceuticals. For instance, the compound can be processed to give pellets, granule, powder, capsule, suspension, injection, suppository, and the like.

For the preparation of these pharmaceuticals, ordinary additives such as vehicles, disintegrators, binders, lubricants, dyes, and diluents. As the vehicles, lactose, D-mannitol, crystalline cellulose, and glucose can be mentioned. Further, there can be mentioned starch and carboxymethylcellulose calcium (CMC-Ca) as the disintegrators, magnesium stearate and talc as the lubricants, and hydroxypropylcellulose (HPC), gelatin and polyvinylpirrolidone (PVP) as the binders. The preparation of an injection can be made using solvents, stabilizers, dissolution-aids, suspensions, emulsifiers, soothing agents, buffers, or preservatives.

The compound of the invention can be administered to an adult generally in an amount of approx. 0.01 mg to 100 mg a day by parenteral administration and 1 mg to 2,000 mg a day by oral administration. The dosage can be adjusted in consideration of age and conditions of the patient.

The present invention is further described by the following non-limiting examples.

EXAMPLES

Example 1

5-[3-(1H-Tetrazol-5-yl)phenyl]-1H-naphtho[1,2-b][1,4]diazepine-2,4(3H,5H)-dione (1) 3-(1-Nitro-2-naphthylamino)benzonitrile A solution of 1-nitro-2-naphthylamine (875 mg, 4.65 mmol), 3-bromobenzonitrile (846 mg, 4.65 mmol), cesium carbonate (3.03 g, 9.30 mmol), tris(dibenzylideneacetone)dipalladium(0) (213 mg, 0.23 mmol) and (+/−)-2,2'-bis(diphenylphosphino)-1,1'-binaphthyl (217 mg, 0.35 mmol) in toluenene (10 mL) was heated at 110° C. for 16 hours. The reaction mixture was poured into a saturated aqueous sodium bicarbonate solution, and was extracted with ethyl acetate. The organic layer was washed with saturated brine, dried over anhydrous sodium sulfate. The solvent was removed under reduced pressure. The residue was purified by silica gel column chromatography (hexane/ethyl acetate=4/1), to give the titled compound (503 mg, yield 37%).

$^1$H-NMR (CDCl$_3$, 400 MHz) δ: 7.37 (1H, d, J=9 Hz), 7.4-7.6 (5H, m), 7.66 (1H, t, J=8 Hz), 7.78 (1H, d, J=8 Hz), 7.86 (1H, d, J=9 Hz), 8.38 (1H, d, J=9 Hz), 8.98 (1H, s).

(2) 3-(1-Amino-2-naphthylamino)benzonitrile 3-(1-Nitro-2-naphthylamino)benzonitrile (1.16 g, 3.99 mmol) was hydrogenated in methanol (20 mL)/THF (40 mL) for 4 hours at room temperature using 10% palladium-carbon (220 mg) as a catalyst. After removal of the catalyst by filtration, the filtrate was concentrated to dryness. The residue was purified by silica gel column chromatography (chloroform/methanol=99/1), to give the titled compound as a yellow crystal (968 mg, yield 93%).

$^1$H-NMR (CDCl$_3$, 400 MHz) δ: 4.38 (2H, br s), 5.45 (1H, br s), 6.87 (2H, s), 7.06 (1H, d, J=7 Hz), 7.2-7.4 (3H, m), 7.4-7.5 (2H, m), 7.8-7.9 (2H, m).

(3) 5-(3-Cyanophenyl)-1H-naphtho[1,2-b][1,4]diazepin-2,4(3H,5H)-dione

To an ice-cold solution of 3-(1-amino-2-naphthylamino)benzonitrile (968 mg, 3.73 mmol) in toluene (10 mL) was added malonyl chloride (436 μL, 4.48 mmol). The mixture was stirred at 80° C. for 20 minutes, then at 110° C. for 10 minutes. After the reaction mixture was cooled to room temperature, the solution part of the reaction mixture was poured into a saturated aqueous sodium bicarbonate solution, and was extracted with ethyl acetate. The organic layer was dried over anhydrous sodium sulfate, and the solvent was removed under reduced pressure. While The precipitated solid in the reaction mixture was dissolved in chloroform, was washed with a saturated aqueous sodium bicarbonate solution, and saturated brine. After drying over anhydrous sodium sulfate, the solvent was removed under reduced pressure. The residues were combined, and Each product purified by silica gel column chromatography (hexane/ethyl acetate=1/4), and the residue was recrystallized from ethyl acetate to give the titled compound as a pale yellow crystal (335 mg, yield 27%). mp: 220-222° C.

$^1$H-NMR (CDCl$_3$, 400 MHz) δ: 3.63 (2H, s), 6.93 (1H, d, J=9 Hz), 7.5-7.7 (6H, m), 7.73 (1H, t, J=7 Hz), 7.89 (1H, d, J=8 Hz), 8.10 (1H, d, J=9 Hz), 8.61 (1H,$).

IR(cm$^{-1}$, KBr): 3238, 2931, 2229, 1693, 1628, 1601, 1583, 1512, 1483, 1460, 1423, 1362, 1309, 1263, 1122, 993, 958, 899, 866, 816, 795, 769, 708, 679, 604, 565, 523, 492, 476, 432.

(4) 5-[3-(1H-Tetrazol-5-yl)phenyl]-1H-naphtho[1,2-b][1,4]diazepin-2,4(3H,5H)-dione To a solution of 5-(3-cyanophenyl)-1H-naphtho[1,2-b][1,4]diazepin-2,4(3H,5H)-dione (150 mg, 0.458 mmol) in toluene (2 mL)/DMF (0.5 mL) was added tri-n-butyltinazido (252 □L, 0.916 mmol). The mixture was stirred at 110° C. for 16 hours, cooled to room temperature. The resultant mixture was acidified with 1M hydrochloric acid, and extracted with chloroform. The organic layer was dried over anhydrous sodium sulfate, and the solvent was removed under reduced pressure. The residue was purified by silica gel column chromatography (chloroform/methanol=9/1), and the residue was recrystallized from ethyl acetate/hexane. The crystal was dried in vacuo at 50° C. for 1 hour, to give the titled compound as a pale yellow crystal (137 mg, 78%).

$^1$H-NMR (CDCl$_3$, 400 MHz) δ: 3.6-3.7 (2H, m), 6.68 (1H, s), 6.80 (1H, d, J=9 Hz), 7.16 (1H, t, J=8 Hz), 7.5-7.6 (2H, m), 7.67 (1H, t, J=8 Hz), 7.8-7.9 (3H, m), 8.34 (1H, d, J=9 Hz), 10.70 (1H, br s), 14.58 (1H, br s).

Example 2

5-[3-(1H-Tetrazol-5-yl)phenyl]-1H-naphtho[1,2-b][1,4]diazepin-2,4(3H,5H)-dione potassium salt To the solution of 5-[3-(1H-tetrazol-5-yl)phenyl]-1H-naphtho[1,2-b][1,4]diazepin-2,4(3H,5H)-dione (100 mg, 0.270 mmol) in ethanol (2 mL) was added a solution of potassium bicarbonate (27 mg, 0.270 mmol) in water (0.5 mL), and concentrated under reduced pressure. The residue was dissolved in water (10 mL), then washed with chloroform. Aqueous layer was concentrated under reduced pressure, to give the titled compound as a yellow amorphous form (86 mg).

$^1$H-NMR (DMSO-d$_6$, 400 MHz) δ: 3.15 (1H, d, J=12 Hz), 3.70 (1H, d, J=12 Hz), 7.03 (1H, d, J=9 Hz), 7.18 (1H, d, J=9 Hz), 7.45 (1H, t, J=8 Hz), 7.5-7.7 (4H, m), 7.88 (1H, d, J=8 Hz), 7.93 (1H, d, J=8 Hz), 8.27 (1H, d, J=8 Hz), 10.87 (1H, br s).

IR(cm$^{-1}$, KBr): 3803, 3676, 3651, 3568, 2372, 1697, 1655, 1577, 1541, 1508, 1466, 1419, 1375, 1317, 1257, 1190, 1084, 1041, 984, 953, 879, 806, 756, 696, 669, 567, 525, 503, 480, 430.

Example 3

5-[4-(1H-Tetrazol-5-yl)phenyl]-1H-naphtho[1,2-b][1,4]diazepin-2,4(3H,5H)-dione (1) 4-(1-Nitro-2-naphthylamino)benzonitrile The titled compound was prepared in a procedure similar to that of Example 1 (1).

$^1$H-NMR (CDCl$_3$, 400 MHz) δ: 7.25 (2H, d, J=7 Hz), 7.46-7.53 (2H, m), 7.62-7.70 (3H, m), 7.80 (1H, d, J=8 Hz), 7.90 (1H, d, J=9 Hz), 8.28 (1H, d, J=9 Hz), 8.72 (1H, br s).

(2) 4-(1-Amino-2-naphthylamino)benzonitrile

The titled compound was prepared in a procedure similar to that of Example 1 (2).

$^1$H-NMR (CDCl$_3$, 400 MHz) δ: 4.37 (2H, br s), 5.71 (1H, br s), 6.65-6.70 (2H, m), 7.20-7.30 (1H, m), 7.30-7.40 (1H, m), 7.45-7.55 (4H, m), 7.80-7.90 (2H, m).

(3) 5-(4-Cyanophenyl)-1H-naphtho[1,2-b][1,4]diazepin-2,4(3H,5H)-dione

The titled compound was prepared in a procedure similar to that of Example 1 (3).

mp: 241-243° C.

$^1$H-NMR (DMSO-d$_6$, 400 MHz) δ: 3.18 (1H, d, J=12 Hz), 3.76 (1H, d, J=12 Hz), 6.93 (1H, d, J=9 Hz), 7.45 (2H, d, J=8 Hz), 7.60-7.73 (3H, m), 7.90-7.95 (3H, m), 8.28 (1H, d, J=8 Hz), 10.96 (1H, br s).

IR(cm$^{-1}$, KBr): 3236, 3153, 2929, 2231, 1684, 1664, 1599, 1500, 1471, 1423, 1369, 1313, 1255, 1225, 1201, 1176, 1111, 1018, 982, 920, 849, 823, 783, 748, 708, 677, 555, 498, 455, 428.

(4) 5-[4-(1H-Tetrazol-5-yl)phenyl]-1H-naphtho[1,2-b][1,4]diazepin-2,4(3H,5H)-dione The titled compound was prepared in a procedure similar to that of Example 1 (4).

$^1$H-NMR (CD$_3$OD, 400 MHz) δ: 3.38 (1H, d, J=12 Hz), 3.76 (1H, d, J=12 Hz), 7.07 (1H, d, J=9 Hz), 7.48 (2H, d, J=8 Hz), 7.61 (1H, t, J=7 Hz), 7.65-7.77 (2H, m), 7.90 (1H, d, J=8 Hz), 8.11 (2H, d, J=8 Hz), 8.24 (1H, d, J=8 Hz).

Example 4

5-[4-(1H-Tetrazol-5-yl)phenyl]-1H-naphtho[1,2-b][1,4]diazepin-2,4(3H,5H)-dione sodium salt The titled compound was prepared by sodium bicarbonate in a procedure similar to that of Example 2.

mp: 265-268° C.

$^1$H-NMR (DMSO-d$_6$, 400 MHz) δ: 3.16 (1H, d, J=12 Hz), 3.71 (1H, d, J=12 Hz), 7.03 (1H, d, J=9 Hz), 7.21 (2H, d, J=8 Hz), 7.58 (1H, t, J=7 Hz), 7.63-7.70 (2H, m), 7.91 (1H, d, J=8 Hz), 8.01 (2H, d, J=9 Hz), 8.26 (1H, d, J=9 Hz), 10.89 (1H, br s).

IR (cm$^{-1}$, KBr): 3496, 3060, 1689, 1662, 1601, 1529, 1473, 1442, 1427, 1387, 1321, 1286, 1259, 1205, 1140, 1111, 1041, 1014, 985, 879, 854, 816, 748, 721, 679, 540, 503, 444.

Example 5

1-Methyl-5-[3-(1H-tetrazol-5-yl)phenyl]-1H-naphtho[1,2-b][1,4]diazepin-2,4(3H,5H)-dione and 1,3-Dimethyl-5-[3-(1H-tetrazol-5-yl)phenyl]-1H-naphtho[1,2-b][1,4]diazepin-2,4(3H,5H)-dione (1) 5-(3-Cyanophenyl)-1-methyl-1H-naphtho[1,2-b][1,4]diazepin-2,4(3H,5H)-dione and 5-(3-Cyanophenyl)-1,3-dimethyl-1H-naphtho[1,2-b][1,4]diazepin-2,4(3H,5H)-dione To a water-cooled solution of 5-(3-cyanophenyl)-1H-naphtho[1,2-b][1,4]diazepin-2,4(3H,5H)-dione (98 mg, 0.30 mmol) in DMSO (1 mL) was added 50-72% sodium hydride (12 mg). The mixture was stirred at room temperature for 1 hour, to which was added iodomethane (0.06 mL, 1 mmol). The mixture was stirred for 4 hours at room temperature, to which was added 50-72% sodium hydride (6 mg) and iodomethane (0.03 mL, 0.5 mmol). The mixture was stirred at room temperature for 18 hour, treated with cold water, and extracted with ethyl acetate. The organic layer was washed with saturated brine, and dried over anhydrous sodium sulfate. The solvent was removed under reduced pressure, and the residue was washed with ethyl acetate, then with hexane, to give 5-(3-cyanophenyl)-1-methyl-1H-naphtho[1,2-b][1,4]diazepin-2,4(3H,5H)-dione as a pale yellow crystal (28 mg, yield 27%). Then the solvent of washings was removed under reduced pressure, and the residue was purified by silica gel column chromatography (hexane/ethyl acetate=1/1), to give 5-(3-cyanophenyl)-1,3-dimethyl-1H-naphtho[1,2-b][1,4]diazepin-2,4(3H,5H)-dione as a pale yellow oil (9 mg, yield 8%).

5-(3-Cyanophenyl)-1-methyl-1H-naphtho[1,2-b][1,4]diazepin-2,4(3H,5H)-dione

FAB-MS (m/z): 342 (M+1)
$^1$H-NMR (CDCl$_3$, 400 MHz) δ: 3.55 (1H, d, J=12 Hz), 3.59 (3H, s), 3.65 (1H, d, J=12 Hz), 6.92 (1H, d, J=9 Hz), 7.5-7.7 (7H, m), 7.89 (1H, d, J=8 Hz), 7.95 (1H, d, J=9 Hz).

5-(3-Cyanophenyl)-1,3-dimethyl-1H-naphtho[1,2-b][1,4]diazepin-2,4(3H,5H)-dione $^1$H-NMR (CDCl$_3$, 400 MHz) δ: 0.84 (3H, d, J=8 Hz), 3.59 (3H, s), 4.10 (1H, q, J=8 Hz), 6.87 (1H, d, J=9 Hz), 7.5-7.7 (7H, m), 7.88 (1H, d, J=8 Hz), 7.94 (1H, d, J=8 Hz).

(2) 1-Methyl-5-[3-(1H-tetrazol-5-yl)phenyl]-1H-naphtho[1,2-b][1,4]diazepin-2,4(3H,5H)-dione The titled compound was prepared from the above-mentioned 5-(3-cyanophenyl)-1-methyl-1H-naphtho[1,2-b][1,4]diazepin-2,4(3H,5H)-dione in a procedure similar to that of Example 1 (4).
$^1$H-NMR (CDCl$_3$, 400 MHz) δ: 3.55 (1H, d, J=12 Hz), 3.60 (3H, s), 3.70 (1H, d, J=12 Hz), 7.02 (1H, d, J=9 Hz), 7.32 (1H, d, J=8 Hz), 7.45 (1H, t, J=8 Hz), 7.57 (1H, t, J=7 Hz), 7.6-7.7 (2H, m), 7.84 (1H, d, J=8 Hz), 7.91 (1H, d, J=9 Hz), 7.96 (1H, d, J=8 Hz), 8.01 (1H, s).

(3) 1,3-Dimethyl-5-[3-(1H-tetrazol-5-yl)phenyl]-1H-naphtho[1,2-b][1,4]diazepin-2,4(3H,5H)-dione The titled compound was prepared from the above-mentioned 5-(3-cyanophenyl)-1,3-dimethyl-1H-naphtho[1,2-b][1,4]diazepin-2,4(3H,5H)-dione in a procedure similar to that of Example 1 (4).
$^1$H-NMR (CDCl$_3$, 400 MHz) δ: 1.51 (3H, d, J=7 Hz), 3.55 (3H, s), 3.71 (1H, q, J=7 Hz), 7.03 (1H, d, J=8 Hz), 7.41 (1H, d, J=8 Hz), 7.51 (1H, t, J=7 Hz), 7.60 (1H, t, J=7 Hz), 7.66 (1H, d, J=8 Hz), 7.70 (1H, d, J=8 Hz), 7.88 (1H, d, J=8 Hz), 7.9-8.0 (3H, m).

Example 6

5-[2-Chloro-5-(1H-tetrazol-5-yl)phenyl]-1H-naphtho[1,2-b][1,4]diazepin-2,4(3H,5H)-dione (1) 4-Chloro-3-(1-nitro-2-naphthylamino)benzonitrile A suspension of 1-nitro-2-naphthyltriflate (1.50 g, 4.67 mmol), 3-amino-4-chlorobenzonitrile (1.05 g, 6.87 mmol), potassium carbonate (645 mg, 4.67 mmol), tetrakis(triphenylphosphine)palladium(0) (162 mg, 0.14 mmol) and triphenylphosphine (65 mg, 0.47 mmol) in toluene (45 mL) was stirred at 110° C. for 16 hours. The reaction mixture was cooled to room temperature, and filtered. The filtrate was diluted with chloroform, washed with 0.2M hydrochloric acid, a saturated aqueous sodium bicarbonate solution and saturated brine. The organic layer was dried over anhydrous sodium sulfate. The solvent was removed under reduced pressure, and the residue was purified by silica gel column chromatography (hexane/ethyl acetate=1/1), to give the titled compound (900 mg, yield 60%).
$^1$H-NMR (CDCl$_3$, 400 MHz) δ: 7.31 (1H, dd, J=2, 8 Hz), 7.44 (1H, d, J=9 Hz), 7.52 (1H, t, J=8 Hz), 7.58 (1H, d, J=8 Hz), 7.62 (1H, d, J=1 Hz), 7.68 (1H, m), 7.84 (1H, d, J=8 Hz), 7.96 (1H, d, J=9 Hz), 8.25 (1H, d, J=9 Hz), 8.67 (1H, br s).

(2) 4-Chloro-3-(1-amino-2-naphthylamino)benzonitrile

The titled compound was prepared in a procedure similar to that of Example 1 (2).
$^1$H-NMR (CDCl$_3$, 400 MHz) δ: 4.40 (2H, br s), 6.01 (1H, br s), 6.68 (1H, d, J=2 Hz), 6.99 (1H, dd, J=2, 8 Hz), 7.18 (1H, d, J=8 Hz), 7.35 (1H, d, J=9 Hz), 7.43 (1H, d, J=8 Hz), 7.5-7.6 (2H, m), 7.8-7.9 (2H, m).

(3) 5-(2-Chloro-5-cyanophenyl)-1H-naphtho[1,2-b][1,4]diazepin-2,4(3H,5H)-dione

The titled compound was prepared in a procedure similar to that of Example 1 (3).
$^1$H-NMR (CDCl$_3$, 400 MHz) δ: 3.6-3.7 (2H, m), 6.8-7.0 (1H, m), 7.2-8.2 (8H, m), 8.2-8.6 (1H, m).

(4) 5-[2-Chloro-5-(1H-tetrazol-5-yl)phenyl]-1H-naphtho[1,2-b][1,4]diazepin-2,4(3H,5H)-dione The titled compound was prepared in a procedure similar to that of Example 1 (4).
$^1$H-NMR (DMSO-d$_6$, 400 MHz) δ: 3.1-3.4 (1H, m), 3.82, 3.86 (1H, d each, J=12 Hz), 6.96, 7.10 (1H, d each, J=9 Hz), 7.5-8.6 (7H, m), 8.24, 8.30 (1H, d each, J=8 Hz), 10.9-11.1 (1H, m).

Example 7

5-[2-Chloro-5-(1H-tetrazol-5-yl)phenyl]-1H-naphtho[1,2-b][1,4]diazepin-2,4(3H,5H)-dione sodium salt The titled compound was prepared by sodium bicarbonate in a procedure similar to that of Example 2.
$^1$H-NMR (DMSO-d$_6$, 400 MHz) δ: 3.18, 3.21 (1H, d each, J=12 Hz), 3.78, 3.80 (1H, d each, J=12 Hz), 6.98, 7.08 (1H, d each, J=9 Hz), 7.4-8.4 (5H, m), 7.90 (1H, d, J=8 Hz), 8.0-8.1 (1H, m), 8.23, 8.26 (1H, d each, J=9 Hz), 10.96 (1H, br s).

Example 8

5-[2-Methyl-5-(1H-tetrazol-5-yl)phenyl]-1H-naphtho[1,2-b][1,4]diazepin-2,4(3H,5H)-dione The titled compound was prepared in a procedure similar to that of Example 6 (1)-(4).
$^1$H-NMR (DMSO-d$_6$, 400 MHz) δ: 1.77 (1.5H, s), 2.47 (1.5H, s), 3.1-3.3 (1H, m), 3.81 (0.5H, d, J=12 Hz), 3.86 (0.5H, d, J=12 Hz), 6.88 (0.5H, d, J=9 Hz), 7.11 (0.5H, d, J=9 Hz), 7.40 (0.5H, s), 7.51 (0.5H, d, J=8 Hz), 7.5-7.8 (3H, m), 7.92 (1H, d, J=8 Hz), 7.9-8.1 (1H, m), 8.2-8.3 (2H, m), 10.96 (0.5H, br s), 11.03 (0.5H, br s).

Example 9

5-[2-Methyl-5-(1H-tetrazol-5-yl)phenyl]-1H-naphtho[1,2-b][1,4]diazepin-2,4(3H,5H)-dione sodium salt The titled compound was prepared by sodium bicarbonate in a procedure similar to that of Example 2.
$^1$H-NMR (DMSO-d$_6$, 400 MHz) δ: 1.70 (1.5H, s), 2.32 (1.5H, s), 3.19 (1H, d, J=12 Hz), 3.78 (0.5H, d, J=12 Hz), 3.80

(0.5H, d, J=12 Hz), 6.91 (0.5H, d, J=9 Hz), 7.11 (0.5H, d, J=9 Hz), 7.2-7.3 (1H, m), 7.44 (0.5H, d, J=8 Hz), 7.5-7.7 (3H, m), 7.8-8.0 (2H, m), 8.18 (0.5H, s), 8.25 (1H, t, J=8 Hz), 10.96 (1H, br s).

Example 10

5-[2-Bromo-5-(1H-tetrazol-5-yl)phenyl]-1H-naphtho[1,2-b][1,4]diazepin-2,4(3H,5H)-dione The titled compound was prepared in a procedure similar to that of Example 6 (1)-(4).
$^1$H-NMR (DMSO-$d_6$, 400 MHz) δ: 3.20 (1H, d, J=12 Hz), 3.76 (1H, d, J=12 Hz), 7.07 (1H, d, J=9 Hz), 7.5-7.9 (5H, m), 7.94 (1H, d, J=8 Hz), 8.20 (1H, s), 8.30 (1H, d, J=8 Hz), 10.94 (1H, s).

Example 11

5-[3-(2-Methyl-2H-tetrazol-5-yl)phenyl]-1H-naphtho[1,2-b][1,4]diazepin-2,4(3H,5H)-dione and 5-[3-(1-Methyl-1H-tetrazol-5-yl)phenyl]-1H-naphtho[1,2-b][1,4]diazepin-2,4(3H,5H)-dione To a solution of 5-[3-(1H-tetrazol-5-yl)phenyl]-1H-naphtho[1,2-b][1,4]diazepin-2,4(3H,5H)-dione potassium salt (123 mg, 0.30 mmol) in DMSO (3 mL) was added iodomethane (0.09 mL, 1.5 mmol). The reaction mixture was stirred at room temperature for 64 hours, to which was added 1M hydrochloric acid, and extracted with ethyl acetate. The organic layer was washed with saturated brine, dried over anhydrous sodium sulfate. The solvent was removed under reduced pressure, and the residue was purified by silica gel column chromatography (hexane/ethyl acetate=1/2-1/3). The crude dione was obtained from fractions (hexane/ethyl acetate=1/2) as a pale yellow crystal, which was recrystallized from ethyl acetate/hexane, to give the above-mentioned compound (57 mg, yield 50%). mp: 252-254° C.
$^1$H-NMR (CDCl$_3$, 400 MHz) δ: 3.64 (2H, s), 4.36 (3H, s), 7.06 (1H, d, J=9 Hz), 7.46 (1H, d, J=8 Hz), 7.5-7.7 (3H, m), 7.71 (1H, t, J=8 Hz), 7.85 (1H, d, J=8 Hz), 7.97 (1H, s), 8.08 (1H, d, J=8 Hz), 8.13 (1H, d, J=8 Hz), 8.34 (1H, s).
IR(cm$^{-1}$, KBr): 3188, 3070, 3022, 2933, 1697, 1662, 1579, 1522, 1462, 1421, 1383, 1306, 1259, 1207, 1113, 1053, 1014, 985, 949, 870, 820, 748, 723, 692, 640, 565, 521, 488, 436.
And then, 5-[3-(1-methyl-1H-tetrazol-5-yl)phenyl]-1H-naphtho[1,2-b][1,4]diazepin-2,4(3H,5H)-dione was obtained from fractions (hexane/ethyl acetate=1/3) as a white crystal (18 mg, yield 16%).
$^1$H-NMR (CDCl$_3$, 400 MHz) δ: 3.62 (1H, d, J=12 Hz), 3.66 (1H, d, J=12 Hz), 4.19 (3H, s), 7.03 (1H, d, J=9 Hz), 7.41 (1H, d, J=8 Hz), 7.6-7.8 (6H, m), 7.88 (1H, d, J=8 Hz), 8.08 (1H, d, J=9 Hz), 8.30 (1H, s).

Example 12

5-[3-(5-oxo-4H-[1,2,4]oxadiazol-3-yl)phenyl]-1H-naphtho[1,2-b][1,4]diazepin-2,4(3H,5H)-dione (1) 5-[3-(N-Hydroxyamidino)phenyl]-1H-naphtho[1,2-b][1,4]diazepin-2,4(3H,5H)-dione A solution of 5-(3-cyanophenyl)-1H-naphtho[1,2-b][1,4]diazepin-2,4(3H,5H)-dione (37 mg, 0.11 mmol), hydroxylamine hydrochloride (76 mg, 1.1 mmol) and triethylamine (0.16 mL, 1.1 mmol) in THF (0.65 mL)/methanol (1.3 mL) was heated under reflux for 2 hours. The solvent was removed under reduced pressure, and to the residue was added water (4 mL). The precipitated crystal was filtered and washed with water. The crystal was dried in vacuo at 50° C., to give the titled compound as a light gray crystal (36 mg, 91%).
$^1$H-NMR (DMSO-$d_6$, 400 MHz) 3.16 (1H, d, J=12 Hz), 3.73 (1H, d, J=12 Hz), 5.83 (2H, br s), 7.00 (1H, d, J=9 Hz), 7.34 (1H, d, J=8 Hz), 7.4-7.5 (2H, m), 7.6-7.7 (4H, m), 7.92 (1H, d, J=8 Hz), 8.26 (1H, d, J=8 Hz), 9.64 (1H, s), 10.92 (1H, s).

(2) 5-[3-(5-Oxo-4H-[1,2,4]oxadiazol-3-yl)phenyl]-1H-naphtho[1,2-b][1,4]diazepin-2,4(3H,5H)-dione To a suspension of 5-[3-(N-hydroxyamidino)phenyl]-1H-naphtho[1,2-b][1,4]diazepin-2,4(3H,5H)-dione (36 mg, 0.1 mmol) in dichloromethane (18 mL) was added pyridine (0.012 mL, 0.15 mmol) and phenyl chlorocarbonate (0.016 mL, 0.13 mmol). The reaction mixture was stirred at room temperature for 1.5 hours, and cold water was added. After the mixture was stirred for 20 min, the organic layer was washed with saturated brine, dried over anhydrous sodium sulfate, and the solvent was removed under reduced pressure. A suspension of the obtained pale yellow crystal in acetonitrile (10 mL) was added 1,8-diazabicyclo[5,4,0]-7-undecene (0.03 mL, 0.2 mmol), stirred at room temperature for 15 minuets. After the solvent was removed, the residue was purified by silica gel column chromatography (chloroform/methanol=10/1) to give a pale yellow crystal. The crystal was washed with chloroform to give the titled compound as white crystal (20 mg, yield 52%).
$^1$H-NMR (DMSO-$d_6$, 400 MHz) δ: 3.19 (1H, d, J=12 Hz), 3.77 (1H, d, J=12 Hz), 6.99 (1H, d, J=9 Hz), 7.5-7.8 (6H, m), 7.81 (1H, d, J=8 Hz), 7.94 (1H, d, J=8 Hz), 8.29 (1H, d, J=9 Hz), 10.96 (1H, s), 12.98 (1H, br s).

Example 13

5-[3-(5-Thioxo-4H-[1,2,4]oxadiazol-3-yl)phenyl]-1H-naphtho[1,2-b][1,4]diazepin-2,4(3H,5H)-dione To an ice-cold solution of 5-[3-(N-hydroxyamidino)phenyl]-1H-naphtho[1,2-b][1,4]diazepin-2,4(3H,5H)-dione (310 mg, 0.94 mmol) and 1,8-diazabicyclo[5,4,0]-7-undecene (561 □L, 3.75 mmol) in acetonitrile (5.7 mL) was added dropwise, a solution of thiocarbonyldiimidazole (251 mg, 1.41 mmol) in acetonitrile (6 mL). The mixture was stirred at room temperature for 1.5 hours, to which was added 1M hydrochloric acid, and extracted with chloroform. The organic layer was washed with saturated brine, dried over anhydrous sodium sulfate. The solvent was removed under reduced pressure, and the residue was purified by silica gel column chromatography (hexane/ethyl acetate=1/1~0/1), to give the titled compound (161 mg, yield 41%).
$^1$H-NMR (DMSO-$d_6$, 400 MHz) δ: 3.18 (1H, d, J=12 Hz), 3.76 (1H, d, J=12 Hz), 7.00 (1H, d, J=9 Hz), 7.5-7.8 (6H, m), 7.87 (1H, d, J=8 Hz), 7.93 (1H, d, J=8 Hz), 8.27 (1H, d, J=9 Hz), 10.94 (1H, br s).

Example 14

5-[3-(5-Thioxo-4H-[1,2,4]oxadiazol-3-yl)phenyl]-1H-naphtho[1,2-b][1,4]diazepin-2,4(3H,5H)-dione sodium salt To the solution of 5-[3-(5-thioxo-4H-[1,2,4]oxadiazol-3-yl)phenyl]-1H-naphtho[1,2-b][1,4]diazepin-2,4(3H,5H)-dione (83 mg, 0.20 mmol) in ethanol (8.7 mL) was added a solution of 0.01M sodium hydroxide (19.5 mL), stirred at room temperature for 10 minutes. The reaction mixture was concentrated under reduced pressure, to give the titled compound (89 mg, quantitative).

$^1$H-NMR (DMSO-$d_6$, 400 MHz) δ: 3.17 (1H, d, J=12 Hz), 3.73 (1H, d, J=12 Hz), 7.02 (1H, d, J=9 Hz), 7.37 (1H, d, J=7 Hz), 7.5-7.8 (5H, m), 7.83 (1H, d, J=8 Hz), 7.92 (1H, d, J=8 Hz), 8.25 (1H, d, J=9 Hz), 10.88 (1H, br s).

Example 15

5-[3-(Oxazol-2-yl)phenyl]-1H-naphtho[1,2-b][1,4]diazepin-2,4(3H,5H)-dione (1) 1-Nitro-N-[3-(oxazol-2-yl)phenyl]-2-naphthylamine The titled compound was prepared from 1-nitro-2-naphthyltriflate and 3-(oxazol-2-yl)aniline in a procedure similar to that of example 6 (1).

$^1$H NMR (CDCl$_3$, 400 MHz) δ: 7.26 (1H, s), 7.35 (1H, d, J=8 Hz), 7.3-7.5 (2H, m), 7.52 (1H, t, J=8 Hz), 7.64 (1H, t, J=8 Hz), 7.7-7.8 (2H, m), 7.80 (1H, d, J=9 Hz), 7.91 (1H, d, J=8 Hz), 7.97 (1H, s), 8.50 (1H, d, J=9 Hz), 9.40 (1H, s).

(2) $N^2$-[3-(Oxazol-2-yl)phenyl]naphthalen-1,2-diamine

The titled compound was prepared in a procedure similar to that of example 1 (2).

$^1$H-NMR (DMSO-$d_6$, 400 MHz) δ: 5.38 (2H, s), 6.7-6.9 (1H, m), 7.1-7.3 (5H, m), 7.3-7.5 (2H, m), 7.63 (1H, s), 7.7-7.8 (1H, m), 8.10 (1H, s), 8.1-8.2 (1H, m).

(3) 5-[3-(Oxazol-2-yl)phenyl]-1H-naphtho[1,2-b][1,4]diazepin-2,4(3H,5H)-dione

The titled compound was prepared in a procedure similar to that of example 1 (3).

$^1$H-NMR (DMSO-$d_5$, 400 MHz) δ: 3.19 (1H, d, J=12 Hz), 3.76 (1H, d, J=12 Hz), 7.03 (1H, d, J=9 Hz), 7.3-7.5 (2H, m), 7.5-7.8 (4H, m), 7.82 (1H, s), 7.9-8.0 (2H, m), 8.21 (1H, s), 8.28 (1H, d, J=8 Hz), 10.93 (1H, s).

IR(cm$^{-1}$, KBr): 3282, 1701, 1655, 1599, 1558, 1512, 1473, 1425, 1362, 1311, 1248, 1140, 1107, 1041, 985, 953, 912, 876, 818, 768, 735, 694, 677, 633, 602, 557, 494, 442.

Example 16

5-[3-(1H-Pyrazol-4-yl)phenyl]-1H-naphtho[1,2-b][1,4]diazepin-2,4(3H,5H)-dione (1) 5-(3-Bromophenyl)-1H-naphtho[1,2-b][1,4]diazepin-2,4(3H,5H)-dione The titled compound was prepared from 1-nitro-2-naphthyltriflate and 3-bromoaniline in a procedure similar to that of example 6 (1), example 1 (2) and (3).

$^1$H-NMR (CDCl$_3$, 400 MHz) δ: 3.61 (2H, s), 7.01 (1H, d, J=9 Hz), 7.2-7.3 (2H, m), 7.42 (1H, s), 7.47 (1H, d, J=8 Hz), 7.6-7.7 (2H, m), 7.71 (1H, t, J=8 Hz), 7.87 (1H, d, J=8 Hz), 8.08 (1H, d, J=9 Hz), 8.45 (1H, br s).

(2) 5-[3-(1H-Pyrazol-4-yl)phenyl]-1H-naphtho[1,2-b][1,4]diazepin-2,4(3H,5H)-dione A suspension of 5-(3-bromophenyl)-1H-naphtho[1,2-b][1,4]diazepin-2,4(3H,5H)-dione (96 mg, 0.25 mmol), 1-(tert-butoxycarbonyl)-1H-pyrazole-4-boronic acid pinacol ester (88 mg, 0.30 mmol), tetrakis(triphenylphosphine)palladium(0) (15 mg, 0.013 mmol), 2M aqueous potassium carbonate solution (0.38 mL) in toluene (7 mL)/ethanol (3 mL) was heated under reflux for 4 hours under $N_2$ atmosphere. The reaction mixture was cooled to room temperature, and filtered. The filtrate was diluted with ethyl acetate, washed with water, and saturated brine. The organic layer was dried over anhydrous sodium sulfate. The solvent was removed under reduced pressure, to give the brown crystal (125 mg). The crystal was washed with ethyl acetate, with hexane, and then with chloroform, to give the titled compound as a gray crystal (65 mg, 72%). mp: >280° C.

$^1$H-NMR (DMSO-$d_6$, 400 MHz) δ: 3.18 (1H, d, J=12 Hz), 3.72 (1H, d, J=12 Hz), 6.98 (1H, d, J=8 Hz), 7.05 (1H, d, J=9 Hz), 7.43 (1H, t, J=8 Hz), 7.53 (1H, s), 7.5-7.7 (4H, m), 7.91 (1H, d, J=7 Hz), 8.21 (1H, s), 8.28 (1H, d, J=8 Hz), 10.89 (1H, s), 12.96 (1H, s).

IR (cm$^{-1}$, KBr): 3236, 2931, 1693, 1666, 1608, 1583, 1514, 1475, 1415, 1381, 1309, 1263, 1200, 1151, 1038, 995, 968, 937, 856, 816, 789, 758, 696, 675, 625, 567, 480, 461, 430, 407.

Example 17

Experimental Procedure

P2X$_4$ receptor antagonism of the compound of the present invention was measured as described below.

1321N1 cells stably expressing human P2X$_4$ receptors were adopted for calcium influx assay. P2X4/1321N1 cells were plated in 96-well assay plate and cultured 24 hours in an atmosphere of 5% $CO_2$ at 37° C. Fura-2 AM calcium indicator dissolved in an extracellular solution for calcium imaging was loaded onto cells for 45 minutes at room temperature. The fluorescence was detected by FLUOstar Optima micro plate reader (BMG labtech). The cells were alternatively illuminated with two excitations wavelengths (340 nm and 380 nm) via xenon lamp and the emitted fluorescence was measured at 510 nm. The fluorescence changes after the treatment of 1 μM ATP were monitored and determined the fluorescence ratio ($F_{240}/F_{380}$) as the index of intracellular calcium change. Tested compound were treated to cells 15 min before the addition of ATP and the inhibition activities of compounds were calculated by comparing the $Ca^{2+}$ response with control in the absence of tested compound.

Experimental Results

TABLE 8

| Test compound | IC$_{50}$ (μM) |
|---|---|
| Example 2 | 0.38 |
| Example 4 | 0.75 |
| Example 15 | 4.2 |
| Example 16 | 3.6 |

As is evident from Table 8, the compounds of the present invention have excellent P2X$_4$ receptor antagonism.

What is claimed is:
1. A method of treating neuropathic pain comprising administering an effective amount of a compound of formula (I) or a pharmacologically acceptable salt thereof to a patient in need thereof:

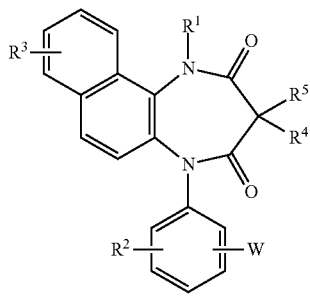

wherein R¹ represents a hydrogen atom, an alkyl group having 1 to 8 carbon atoms, an alkenyl group having 2 to 8 carbon atoms, an alkyl group having 1 to 8 carbon atoms substituted with 1 to 3 halogen atoms, or an alkyl group having 1 to 3 carbon atoms substituted with phenyl;

each of R² and R³ independently represents a hydrogen atom, a halogen atom, hydroxyl, nitro, cyano, amino, carboxyl, carbamoyl, sulfamoyl, an alkyl group having 1 to 8 carbon atoms, an alkoxy group having 1 to 8 carbon atoms, an alkyl group having 1 to 8 carbon atoms substituted with 1 to 3 halogen atoms, an alkoxy group having 1 to 8 carbon atoms substituted with 1 to 3 halogen atoms, an alkylamino group having 1 to 8 carbon atoms, a dialkylamino group having 2 to 8 carbon atoms, an acylamino group having 2 to 8 carbon atoms, an acylamino group having 2 to 8 carbon atoms substituted with 1 to 3 halogen atoms, an alkylsulfonylamino group having 1 to 8 carbon atoms, an acyl group having 2 to 8 carbon atoms, an alkoxycarbonyl group containing an alkoxy moiety having 1 to 8 carbon atoms, an alkylthio group having 1 to 8 carbon atoms, an alkylsulfinyl group having 1 to 8 carbon atoms, or an alkylsulfonyl group having 1 to 8 carbon atoms;

each of R⁴ and R⁵ independently represents a hydrogen atom, an alkyl group having 1 to 8 carbon atoms, an alkyl group having 1 to 8 carbon atoms substituted with 1 to 3 halogen atoms, or an alkyl group having 1 to 3 carbon atoms substituted with phenyl; and W represents tetrazole, 1,2,4-triazole, 1,2,3-triazole, 1,2,4-oxadiazole, pyrazole, imidazole, oxazole, isoxiazole, pyrrole, thiazole, pyridine, or pyrrolidine, and optionally having a substituent selected from the group consisting of a halogen atom, cyano, oxo, thioxo, an alkyl group having 1 to 8 carbon atom, and an alkyl group having 1 to 8 carbon atoms substituted with 1 to 3 halogen atoms.

2. A method of treating neuropathic pain comprising administering an effective amount of a compound of the formula (I) or a pharmacologically acceptable salt thereof described in claim 1 to a patient in need thereof, wherein W represents a five or six membered heterocyclic ring containing 1 to 4 nitrogen atoms as the members of the ring, and optionally having a substituent selected from the group consisting of a halogen atom, cyano, oxo, thioxo, an alkyl group having 1 to 8 carbon atom, and an alkyl group having 1 to 8 carbon atoms substituted with 1 to 3 halogen atoms.

3. A method according to claim 1, wherein W represents tetrazole, 1,2,4-triazole, 1,2,3-triazole, 1,2,4-oxadiazole, pyrazole, or imidazole, and optionally having a substituent selected from the group consisting of a halogen atom, cyano, oxo, thioxo, an alkyl group having 1 to 8 carbon atom, and an alkyl group having 1 to 8 carbon atoms substituted with 1 to 3 halogen atoms.

4. A pharmaceutical composition comprising an effective amount of a compound of the formula (I) or a pharmacologically acceptable salt thereof described in claim 1 and a pharmaceutically acceptable carrier, wherein W represents a five or six membered heterocyclic ring containing 1 to 4 nitrogen atoms as the members of the ring, and optionally having a substituent selected from the group consisting of a halogen atom, cyano, oxo, thioxo, an alkyl group having 1 to 8 carbon atom, and an alkyl group having 1 to 8 carbon atoms substituted with 1 to 3 halogen atoms.

* * * * *